United States Patent [19]

Brown et al.

[11] Patent Number: 4,863,474
[45] Date of Patent: Sep. 5, 1989

[54] SKELETAL IMPLANTS

[75] Inventors: Ian A. Brown; George J. J. Cremore, both of Wiltshire; Peter J. Gibson, Glouscestershire, all of England

[73] Assignee: Zimmer Limited, United Kingdom

[21] Appl. No.: 163,129

[22] Filed: Feb. 23, 1988

Related U.S. Application Data

[63] Continuation of Ser. No. 627,458, Jul. 3, 1984, abandoned.

[30] Foreign Application Priority Data

Jul. 8, 1983 [GB] United Kingdom ................ 8318483

[51] Int. Cl.$^4$ ........................... A61F 2/28; A61F 2/32
[52] U.S. Cl. ......................................... 623/16; 623/23
[58] Field of Search ...................... 623/16, 18, 20, 21, 623/22, 23

[56] References Cited

U.S. PATENT DOCUMENTS 3,067,740 12/1962 Haboush ............................... 623/23

FOREIGN PATENT DOCUMENTS 0038902 11/1981 European Pat. Off. ............. 623/23

Primary Examiner—Richard J. Apley
Assistant Examiner—David J. Isabella
Attorney, Agent, or Firm—Richard H. Brink

[57] ABSTRACT

This invention relates to a skeletal implant designed to provide a structure which bone can fill so as to biologically anchor the implant in position. A series of cutting edges are aligned on at least part of the surface and directed in a direction of relative movement between implant and bone. Bone removed by these edges is urged into a series of interconnecting spaces beneath the surface. Preferably a porous surface and the cutting edges are provided by perforated microcontoured sheet material. The three dimensional porosity formed by the perforations and contours results in bone debris impacted into the voids particularly at the time of implantation which will subsequently become integral with surrounding bone.

7 Claims, 4 Drawing Sheets

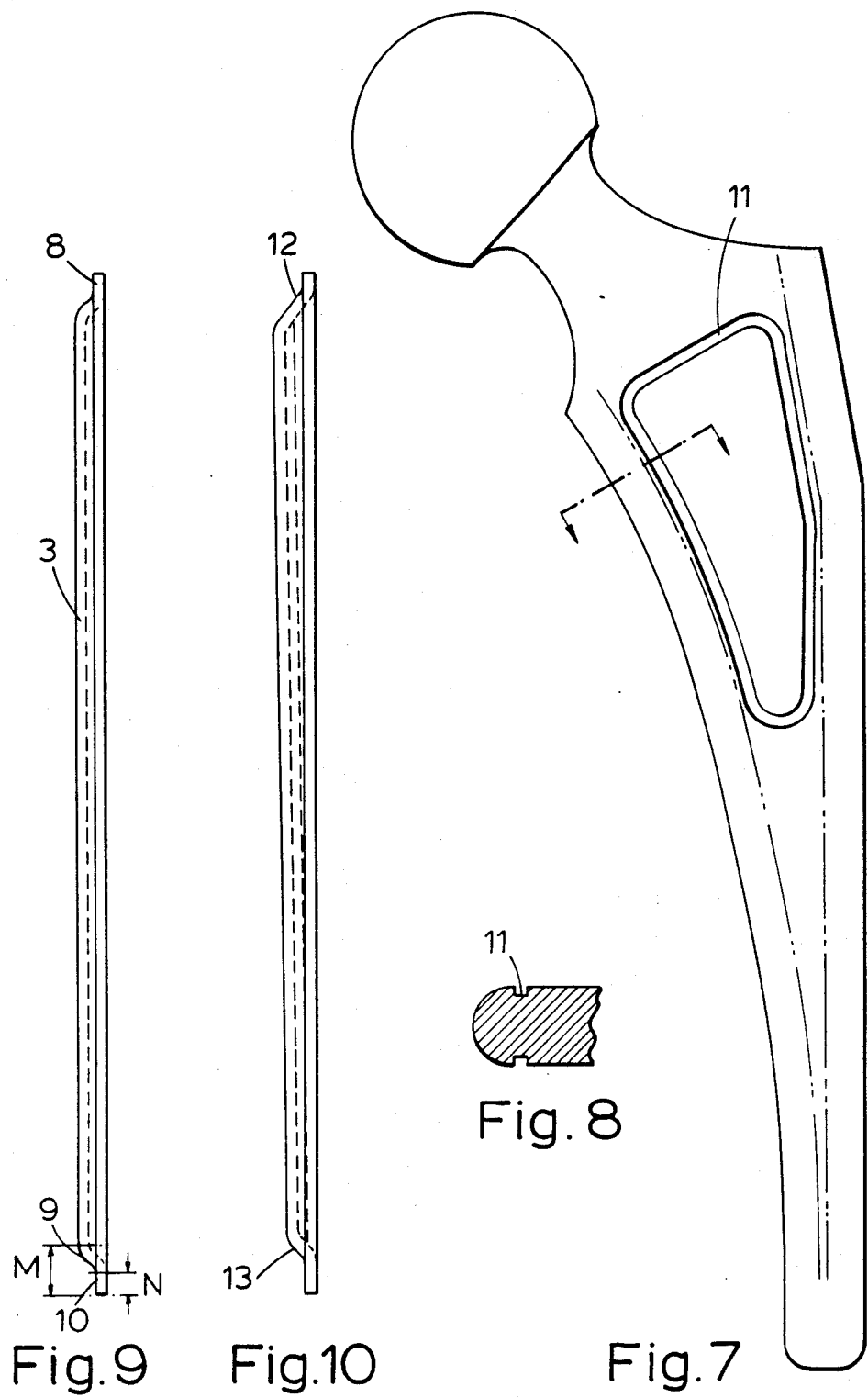

SKELETAL IMPLANTS

This is a continuing application of application Ser. No. 627,458 filed July 3, 1984, now abandoned.

This invention relates to skeletal implants.

The fixation of permanent skeletal implants was achieved in the early years by a wedge fit of smooth surfaced implants into the intra medullary canal - augmented in some design by macrofenestrations through the cross section to allow bridges of bone to pass through the implant and so improve fixation.

To improve the long term fixation of joint replacement implants the use of bone cement, as a grouting agent between implant and bone, was introduced. However, like all inert materals bone cement has a finite fatigue life and is subject to cracking - especially if the bone structure in contact with it changes with time.

While fixation with bone cement has remained the most common method of implant fixation there has been a continuous search for a system of integrating the implant into the skeletal structure. This biological fixation should provide better stress transfer between bone and implant, and be self repairing should micro-fractures occur.

Previous attempts to provide biological fixation can be divided into three categories:

(a) contours of the implant surface against which the bone can grow to stabilise it against movement;

(b) porous surfaces to allow ingrowth of bone or tissue to interlock with the implant;

(c) bioreactive materials which are surface active in vivo producing a chemical bond between implant and surrounding tissues.

None of these methods have been widely accepted due to problems of reliably achieving implant incorporation and/or special post-operative requirements to ensure implant stability.

Contoured implants have been produced by machining grooves or steps into the surface or by casting either very rough surfaces or surfaces with a layer of beads approximately 1 to 1.5 mm in diameter. Fixation depends on bone ongrowth over the total surface of crevices and asperties.

Macro contoured surfaces have been produced with smooth depressions of 5 to 10 mm across and 2 to 5 mm deep. These valleys have bone chips laid into them at the time of implantation. The bone solidifies later to stabilise the implant. The major disadvantage with bone ongrowth (rather than ingrowth) is that it does not adhere to the implant to transmit tensile loads. Consequently push-pull type of loading on the implant can only be transmitted at the bone interface in compression. This provides less than optimal stress distribution in the bone.

The development of truly porous surfaces systems followed studies which showed the potential for tissue and bone to grow into porous implants. These studies on animals showed the relationship between pore size and the type of tissue ingrowth. The porous fixation systems which have been produced since then have had pores in the range 75 to 350 $\mu$m.

After implantation it has been anticipated that bone will ingrow to fill the porous system. However, clinical evidence has not shown the reliability of this approach.

The porous systems have been comprised of a range of materials in a variety of forms, and produced in different ways.

A porous coating composed of several layers of cobalt chromium alloy spheres (approximately 300$\mu$in dia) was produced by sintering the powder to castings of the same alloy. The spaces between the particles provide the pores for tissue ingrowth. Other powder coatings have been achieved by isostatic compaction and subsequent sintering of particles of cobalt-chromium alloy, titanium, titanium alloy and stainless steel.

Surface layers of wire based pads have provided a porous structure for tissue ingrowth. Random orientated linked short fibres have been fused into porous pads before sintering on to the implant surface. The diameters of the wires and the compaction determine the pore sizes. Wires of titanium, titanium alloy, cobalt base alloy have been used. Similar short fibre systems in stainless steel and titanium have been formed and fused directly to the substrate by isostatic compaction and sintering.

Long length metal fibre systems have been formed using woven wire mesh which is pressure sintered to the substrate. This approach provides: predictable pore size; larger pore size without compromising integrity; low value of surface area to volume ratio, thus limiting the metal ion release. Stainless steel and titanium woven meshes have been described.

Polymer based porous surface coatings have been developed to provide a more compatible mechanical interface (being less resilient to applied load and hence more similar to the properties of bone) as well as a base for tissue ingrowth.

Purely plastic materials with a Swiss cheese type of porous structure have included high density polyethylene and polysulphone. A composite material of short carbon fibres and polytetrafluoroethylene (PTFE) has been used. The porosity is formed by random fibre 'scaffolding' whose integrity is maintained by PTFE 'joints' at the fibre intersections.

In all of the porous systems described to date it has been anticipated that bone will grow into the pores. However, this has not happened so reliably in practice. This may be due to several factors; the size of the pores in relation to possible micromotion of the implant under normal activity loading (pistoning of an amount greater than a 250$\mu$pore size will prevent ingrowth); the potential for bone ingrowth in elderly humans is likely to be less than that of a young laboratory animal.

The high surface area of some porous systems increases the release of metal ions in vivo. This could be a risk with stainless steel and cobalt-chrome alloy. Concern has also been expressed for the release of vanadium and aluminium from titanium alloy where the surface area is great. However, the use of commercially pure titanium avoids this danger.

Bioglasses bonded to the surface of the implant are intended to be reactive only at their interface with the bone such that a chemical bond develops. Calcium phosphate ceramics (particularly hydroxyapatites) and glasses based on $SiO_2$, $Na_2O$, $CaO$, $P_2O_5$ $CaF_2$ have been evaluated.

To produce a good bone bond to the bioglass the level of bioreactivity is critical: too low and micromotion between bone and implant will prevent a bond forming: too high and the micromotion may induce continuous dissolution of the coating. Bioglasses also suffer the disadvantages of low strength and brittleness which could produce cracking on a less resilient implant substrate. Composites of metal fibre reinforced bioglasses have been described. These have greater strength and lower modulus than pure bioglass. However the techniques for their manufacture are complicated and require sophisticated technology.

In summary, there have been three basic approaches to achieve biological fixation of implants but each has distinct disadvantages:

surface contoured implants require immobilisation of the patient for a period of months to allow tissue to ongrow but even then the stress system in the bone is not optimal since only compressive stresses can be transmitted;

porous layered implants have relied on the ability of the bone to integrate into micro pores formed by a variety of sophisticated techniques;

bioreactive layered implants require technically sophisticated techniques and the bond to bone has not proved reliable due to micromotion, and critical bioreactivity, low strength and high modulus of the bioglasses.

There has therefore been a need for an implant surface to provide long term positive adhesion between bone and implant without the need for prolonged patient immobilisation to achieve the attachment.

Such a system should have adequate strength and strength of attachment to the substrate, have reliable filling of the porosity by bone, be simple to produce and bond to the substrate.

According to the invention there is provided a skeletal implant having on at least a portion of the surface of the implanted portion a multiplicity of cutting edges located above intercommunicating spaces beneath the surface and directed in a direction of relative movement between the implant and bone.

The raised or cutting edges stand proud of the surrounding surfaces of the implant. The general planer surface from which the edges extend may also be slightly above the surrounding surface of the implant but can be co-planar or even below the profile of the surface. The effect of the edges is to slightly bulk out the relevant profile of the implant.

The raised or cutting edges of the perforations scoop particles of bone into the spaces when the implant is rubbed against the bone, either manually, or during insertion. Thus at the time of implantation bone already fills the spaces beneath the surface of the implant. These micro-grafts then become integral with the surrounding bone provided that no gross movement occurs between bone and implant. This is achieved by ensuring a good fit, (through shape and size) of the implant to the endosteal cavity or by other means of mechanical stabilisation e.g. bone screws through the implant.

The surface can be a sheet or other planar material disposed on the appropriate area of the implant and with edge portions extending outwardly from the sheet and partially or completely surrounding openings in the surface leading to intercommunicating spaces beneath the surface. The edges could be formed by applying edge members to the openings or by forming edge members by appropriate cutting and bending of the sheet material in or around the openings. The spaces beneath the surface could result from the manner of mounting a sheet on the implant or by reason of grooves or other openings in the body of the implant or by application of the implant of a laminate surface the portion beneath the surface being formed from open celled structure.

If the surface structure of the laminate is porous with interconnecting cells then cutting edge strips can be applied to portions of that surface.

The alignment of the edges will depend on the likely relative movement of implant to bone. Thus the edges can be disposed to urge or scoop portions of bone as the implant enters the bone structure. Alternatively the alignement can be to cause removal of bone as the implant and bone are subjected to torsional forces or tend to rotate in relation to each other. The alignment can also be in the direction of removal of the implant. Thus the edges can not merely urge removed portions of bone into the spaces beneath the surface but also assist in stabilising movement of the implant relative to the bone. Different edges can be differently aligned so as to operate with different directions of relative movement.

The edged surface can be applied to all of the surface of the implant which will be within the bone or only to anchoring or stabilising portions thereof and can be combined with surface portions of other types e.g. contoured surfaces, and areas of bioreactive material.

Thus the edged surface can be wholly or partially coated with a bio-reactive material (for example a bioglass). After implantation the bio-reactive material will assist in producing a bond between the implant and surrounding bone tissues by encouraging intimate contact between bone and implant within the porous material.

In a further development a two or three phase mesh is envisaged. A metal perforated system; pore surfaces lined with bioreactive material to encourage bone apposition; cutting edges made of a biodgradable substance (their purpose is to urge bone in at the time of implantation and subsequently to be resorbed to avoid the cutting edges causing abrasion). The bone urged into the porous system would thus stabilise the implant.

The invention also includes a sheet material having openings therein and edge portions located thereon to urge bone material through said openings which material is shaped and adapted for application to a skeletal implant whereby after application to the implant spaces will be left which connect with the opening and each other.

In a preferred embodiment of the invention the surface of the implant is formed from a contoured mesh. This mesh can be applied as a coating to a surface of the implant to provide the edges and underlying interconnecting spaces.

Thus the contoured mesh coating is composed of a contoured perforated sheet or sheets of a biocompatible material bonded to the surface of a skeletal implant.

In the preferred configuration a perforated mesh of commercially pure titanium is resistance welded or diffusion bonded to implants of titanium alloy. A range of other materials for both components and methods of attachment also employed would be readily apparent to one skilled in the art.

The structure of the invention and particularly in its preferred embodiment offers advantages over previously disclosed systems, it has a three dimensional porous structure thus providing adhesion between bone and implant which contoured implants do not have;

it incorporates micro bone grafts at the time of implantation thus maximising chances of boney integration of the implant - which is not provided by any other porous implant;

it offers a greater void volume for bone within its interstices than sintered particle coatings and comparable to some wire systems thus providing greater strength of bone attachment and improving the chances of viable bone forming and remaining indefinitely;

the mesh, being formed from a sheet, has greater structural integrity than sintered particles or wire systems;

the method of manufacture of the mesh and its method of attachment are based on relatively simple conventional methods.

Expanded metal mesh is well known in different materials for a variety of commercial applications. In the preferred technique the mesh is produced by conventional methods of manufacturing expanded metal e.g. perforation, contouring and expansion by drawing in two directions to open the pores. Typically the mesh can be formed from sheet of 0.5-0.76 mm (20-30 thousandths inch) thickness (20-30 standard wire gauge).

Commercially pure titanium is preferred as this has proven biocompatibility with no potentially toxic minor alloy constituents which could leach out over a long period from the increased surface area.

However, it is envisaged that other biocompatible metals could be used though not optimal e.g. stainless steel, cobalt chrome alloy. The perforations take the form of scoop like apertures arranged in overlapping parallel arrays. The perforations are arranged so that the implantation process and any subsequent 'settling' into the bone due to patient activity loading will cause bone to be scooped and impacted into the pores.

The invention will now be illustrated more specifically in the accompanying drawings in which:

FIG. 7 is a view of a skeletal implant with groove for reception of a flagned mesh.

FIG. 8 is a partial cross section on line 8—8 of FIG. 7.

FIG. 9 is a cross section of the modified version of FIG. 6.

FIG. 10 is a further modification of this version of FIG. 6.

Figure 1:
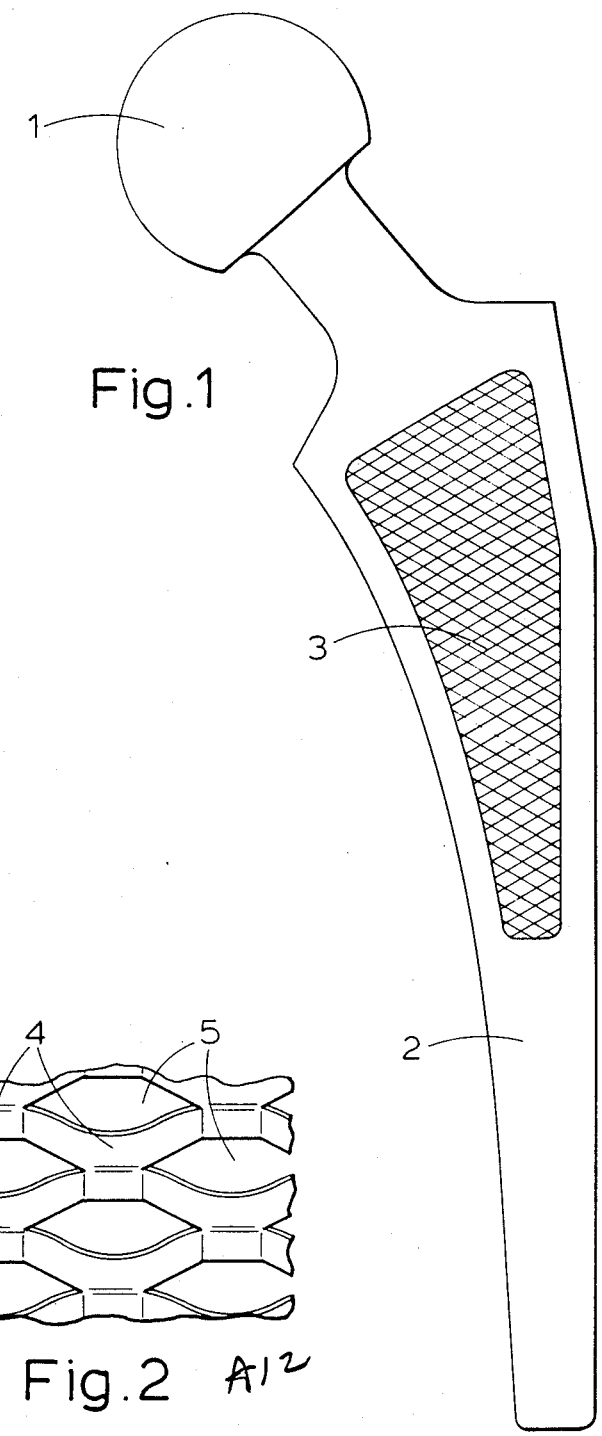
FIG. 1 is a skeletal implant with edged surfaces.
Figure 2:
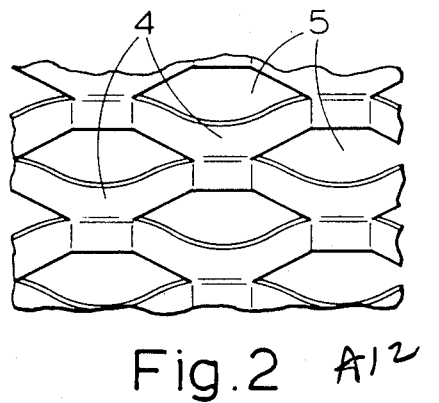
FIG. 2 is a view of the mesh structure.

In FIG. 1 there is shown a skeletal implant 1 with a portion 2 for insertion into an opening in a skeletal member. On part of the surface of said portion there are disposed shaped portions 3 of a commercially available expanded metal mesh of thickness 0.56 mm (22 S.W.G.).

These mesh surface portions have edges 4 aligned to cut along the direction of insertion of the implant as it moves into a bone opening in the skeletal member; the spacing between the partially overlapped parallel rows of apertures can be 2 mm.

The depth of the ripple (C in FIG. 3) is approximately 1mm and the distance peak to peak between parallel rows of ripples is 6 mm.

Figure 3:
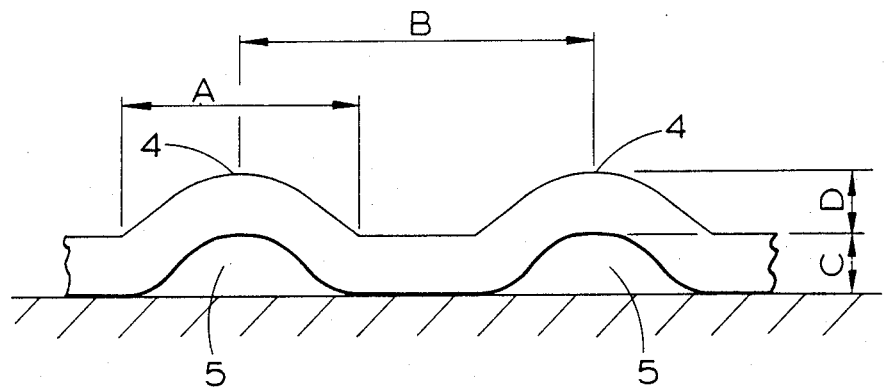
FIG. 3 is a cross section through a surface portion of the implant (i.e. the mesh)

As shown in FIG. 3 the distance between perforations or edges 4 (apex to apex) on a given row (B in FIG. 3) is 6 mm.

The edges 4 are individual scoop-like perforations which are 3 mm wide (Distance A in FIG. 3) with the curved lip raised 1 mm at its apex (Distance C see FIG. 3).

Figure 4:
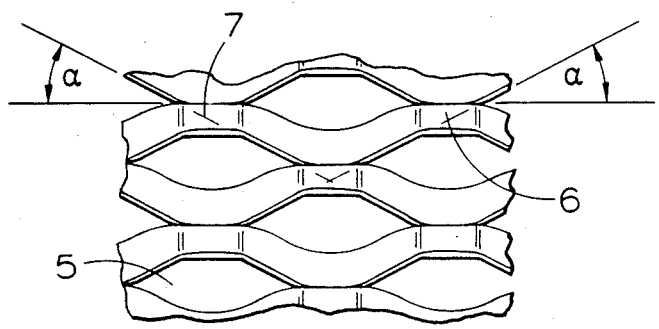
FIG. 4 is a view of an underside of a mesh surface for application to an implant.

The underside of the mesh as shown in FIG. 4, in contact with the substrate is also contoured e.g. by two systems of intersecting furrows 6, 7 to create the underlying spaces 5. These furrows are inclined at an angle α approximately 30° to the direction of the rows of the apertures. This system of intersecting furrows forms interconnections between apertures under the bridges between apertures i.e. a three dimensional porous system is produced by a single layer bonded to the substrate.

Other structures of mesh and spacings and dimensions can readily be visualised.

Figure 5:
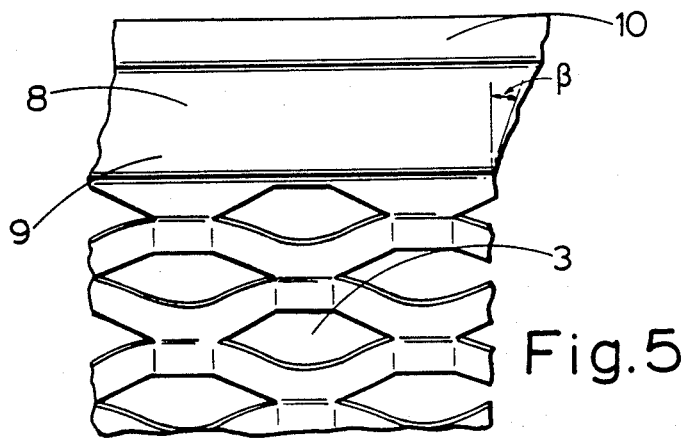
FIG. 5 is a view of a modified version of the mesh.
Figure 6:
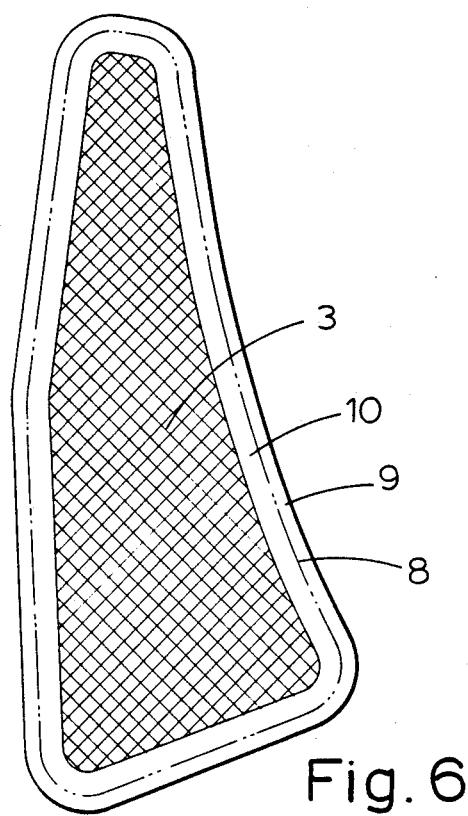
FIG. 6 is a plan view of the modified version.

The mesh can be attached to a skeletal implant base of suitable material by resistance welding. Generally resistance welding or spot welding involves pressing an electrode against the portion of the mesh to be fused to the implant and passing a current through the electrode to melt the materials directly under it. Electrode pressure forces the parts together and when the current is stopped the parts are fused when the weld becomes solid. Generally the mesh portion will be spot welded around the periphery, the spot weld then holding the main part of the mesh against the surface of the implant. In a preferred embodiment of the invention a groove is cut in the implant corresponding to the peripheral profile of the mesh structure or pad to be applied to the implant. The mesh pad is provided with a flange around the periphery of the pad which on application of the pad to the implant locates into the groove. This embodiment is shown in FIGS. 5, 6 and 10. Mesh 3 is provided with a flange 8. The initial portion 9 is at an angle β to the general plane of the mesh. The outermost portion of the flange 10 is co-planar with the general plane of the mesh. The initial portion 9 can be joined to the main body and outer portion of the flange by definitely angled junctures but more usually by curved juncture to the extent that portion 9 can be an S shaped flange. In FIGS. 7 and 8 there is shown an implant with a groove 11 to receive the flange 8 of the mesh. The depth of this groove can be 75% of the thickness of the flange sheet. Generally the width of the groove is greater than outermost portion 10 of the flange so as to accommodate the lower portion of the initial portion 9.

The flange is then spot welded by resistance welding around its periphery in the manner indicated above. The resistance welding reduces the thickness of the sheet to correspond approximately to the depth of the groove. Finally at least the periphery is dressed by manual grinding technique to provide a smooth and more aesthetically satisfying product.

Thus one can have as a "pad" a mesh with a plain (imperforated) periphery which is spot welded to the implant. The edge can be bonded to lie slightly below the profile of the implant. For example the peripheral flange can be 3 mm wide and slightly angled (angle β in FIG. 5) for the initial portion to the plane of the rest of the mesh. The initial portion 9 will be about 2.00 mm wide and the outermost portion 10 (dimension N in FIG. 9) about 1 mm wide to give total width (dimension M in FIG. 9) of 2.5 mm. A groove of 2.5 mm wide and about 0.42 mm deep is cut in the implant (groove 11 in FIGS. 7 and 8) in profile corresponding to that of the flange. The groove accommodates portion 10 and lower part of the portion 9 of the flange. Resistance welding of the flange slightly reduces the thickness of the flange and the flange can be dressed to provide a smooth product.

Particularly where the implant has a skeletal insert section which has parallel sides i.e. is not tapered from insert to outer portion, the lower edges of the anchoring area may effect the removal of bone so the upper or outermost edges are not very effective. In order that the outermost edges may be more effective, the plane of the anchoring portion may be slightly angled in relation to the plane of the relevant portion of the skeletal implant.

Thus in the embodiment of the invention wherein a flanged mesh is employed the angle of the flange to the general plane of the mesh may be increased along a portion of the flange to urge the outermost or upper positions of the mesh slightly outwardly. Thus as the implant is inserted later edges to enter will be slightly more above the general surface of the implant than the preceding edges.

Accordingly the angle of the flange in the flanged embodiment of the mesh may vary around the periphery of the mesh pad.

Other techniques for angling the height of the edges in the anchoring area in relation to the remainder of the implant can readily be visualised for example by altering the depth of the groove or varying the dimensions of the edges.

In FIG. 10 the depth of the flange as created by the angle $\beta$ of portion 9 is greater at the outer portion of the mesh (portion 12 in FIG. 10) than at the inner or lower portion (portion 13). The edges in portion 12 then extend further from the implant than do the edges in portion 13.

Additional welding could be provided for some or all points of contact between the mesh and implant.

The mesh can also be attached to the skeletal implant base by diffusion bonding although the technique is more involved and requires expensive equipment. Thus application by diffusion bonding could be effected as follows:

1. The underside ripple apices are finished lightly to produce flat areas to improve bonding;
2. The bulk titanium alloy implant and the titanium mesh are surface etched in an aqueous solution of hydrofluoric acid (5% by vol) and nitric acid (20% by vol);
3. The mesh and implant are washed in water and dried immediately by immersion in acetone and heating to 80° C. in a vacuum oven;
4. The mesh is assembled against the implant in a fixture which will apply a dead weight load to the mesh with pads of recrystallised alumina or other non reacting material being used to apply the pressure and the applied load is approximately 0.6 Kg/sq. cm of mesh;
5. The assembly is heated in a vacuum furnace (vacuum better than $10^{-4}$ torr) to 925° C. for sintering periods ranging from 1 hour upwards (typically 3 hours); and
6. The assembly is cooled to 500° C. at approximately 10° C. per minute followed by an argon quench.

Attachment strengths of the order of 400 N/CM$^2$ (of total mesh area) are typically obtained by pulling the coating normal to the substrate surface.

In metal systems hot isostatic pressing instead of a dead weight could be used to achieve the diffusion bond. This will be particularly relevant to the coating of curved or multifaceted surface.

The mesh configuration already described is considered to be one of a range. The design and aperture size may need to be tailored to individual implant types and particular bone requirements.

For example the following ranges in dimensions are envisaged as particularly suitable:
aperture width 0.2 mm to 5 mm
aperture height 0.15 mm to 3 mm
row separation 0.2 mm to 4 mm
aperture separation 0.3 mm to 10 mm
ripple height 0.15 mm to 3 mm
ripple separation 0.3 mm to 10 mm The orientation of the apertures may be multidirectional to counteract multidirectional loading, i.e. the scoops may face in one or more directions.

Multiple layers of mesh may be necessary to produce a greater void volume for bone attachment or to provide a low modulus porous layer.

Alternatively, a low modulus layer may be obtained by having the scoop apertures attached at only one side of the aperture. The surface layer so formed would be compliant to forces applied normal to the plane of the porous surface due to the flexing of the scoops.

Lower modulus porous surface layers may also be obtained by the use of low modulus materials for the mesh such as biocompatible plastics or plastic carbon composites. Bonding processes such as by non-biodegradable adhesives could be employed to attach the pads to the substrate.

It is also envisaged that low modulus components with a porous layer, of the form already described, and integral with the main bulk of the implant will be possible through the use of fibre reinforced composites. The main load bearing component of the implant will be made in a high strength low modulus material to withstand normal activity loading and create physiological load distribution in the bone by virtue of is mechanical compatibility. A contoured mesh of a compatible material can then be fused to the surface or portions thereof to provide the necessary edges.

We claim:

1. An implant having an outer engaging surface, for insertion into a skeletal member comprising a porous anchoring means on at least a part of the bone engaging surface of said implant, said porous anchoring means defining a multiplicity of raised cutting edged, said raised cutting edges extending outwardly from said bone engaging surface and forming plurality of openings leading to enter communicating pockets beneath said anchoring means adjacent said bone surface, said cutting edges at least partially surrounding said pockets as being located in relation to said pockets whereby on movement of implant into the skeletal member, said cutting edges removes portion of the bone urges the bone into said pockets.

2. An implant according to claim 1 wherein said anchoring means is a planar member disposed over a portion of the bone engaging surface with said raised cutting edge extending outwardly from the surface of said planar member.

3. An implant accordingly to claim 2 wherein the anchoring means is a perforated sheet wherein said sheet is out and bent to create said raised cutting edges and said pockets.

4. An implant according to claim 2 wherein the anchoring means is a contoured porous mesh.

5. An implant according to claim 4 wherein the anchoring means is a perforated contoured mesh of commercially pure titanium and said implant is a titanium alloy.

6. An implant according to claim 4 wherein the openings having an aperture width of 0.25 mm to 5 mm, an aperture height of 0.15 mm to 3 mm, a row separation of 0.2 mm to 4 mm, an aperture separation of 0.3 mm to 10 mm, a ripple height of 0.15 mm to 3 mm and a ripple separation of 0.3 mm to 10 mm.

7. An implant according claim 4 wherein a flanged edge is provided around the periphery of the mesh, a groove of configuration corresponding to the peripheral outline of the mesh is provided in the implant said flanged edge is disposed within said groove.

* * * * *